US005210241A

United States Patent [19]

Lin

[11] Patent Number: 5,210,241

[45] Date of Patent: May 11, 1993

[54] PROCESS FOR PREPARING COCOA BUTTER EQUIVALENT FROM SEMI-REFINED NONTOXIC CHINESE VEGETABLE TALLOW

[76] Inventor: Yitian Lin, 441 Guang Fu Xi Lu, Shanghai, China

[21] Appl. No.: 815,605

[22] Filed: Jan. 3, 1992

Related U.S. Application Data

[63] Continuation of Ser. No. 388,770, Aug. 2, 1989, abandoned, which is a continuation-in-part of Ser. No. 2,906, Jan. 13, 1987, abandoned.

[30] Foreign Application Priority Data

Jan. 16, 1986 [CN] China ................................ 86100502

[51] Int. Cl.[5] ......................... C07C 1/00; C07B 51/43

[52] U.S. Cl. .......................................... 554/8; 554/19; 554/20; 554/71; 554/72; 554/185; 554/193; 554/208

[58] Field of Search ..................... 260/428.5, 412, 414; 554/208, 185, 193, 8, 19, 20, 71, 76, 72

[56] References Cited

U.S. PATENT DOCUMENTS

| | | | |
|---|---|---|---|
| 3,093,480 | 6/1963 | Arnold | 260/404.5 |
| 4,127,597 | 11/1978 | Craig et al. | 260/404.5 |

FOREIGN PATENT DOCUMENTS

| | | | |
|---|---|---|---|
| 918 | 2/1963 | Japan | 260/428.5 |
| 897841 | 1/1982 | U.S.S.R. | 260/428.5 |

*Primary Examiner*—Jose0 G. Dees
*Assistant Examiner*—Joseph M. Conrad
*Attorney, Agent, or Firm*—Pennie & Edmonds

[57] ABSTRACT

This invention relates to a process of preparing Cocoa Butter Equivalent (CBE) from Chinese Vegetable Tallow (CVT) and to the product prepared. Crude CVT is first subjected to a semi-refining process comprising an alkali treatment, a water wash and an adsorption step. The semi-refined CVT is subjected to a single step fractional crystallization under controlled conditions. After removal of the solvent from the crude CBE found in the mother liquor after filtration, the crude CBE is subjected to a steam distillation process, addition of antioxidants and a final filtration. The resulting product meets all of the criteria necessary for Cocoa Butter Equivalent.

4 Claims, 6 Drawing Sheets

PROCESS FOR PREPARING COCOA BUTTER EQUIVALENT FROM SEMI-REFINED NONTOXIC CHINESE VEGETABLE TALLOW

This application is a continuation of Ser. No. 07/388,770, filed Aug. 2, 1989, now abandoned, which is a continuation-in-part of Ser. No. 07/002,906, filed Jan. 13, 1987, abandoned.

This invention related to a process for preparing oil or fat from an oil-bearing plant. More particularly it relates to the process and technology of preparing Cocoa Butter Equivalent (CBE) from Chinese Vegetable Tallow (CVT).

BACKGROUND OF INVENTION

The CBE prepared from Chinese Vegetable tallow is used as high grade substitute for natural cocoa butter and it may be extensively used in the production of chocolate and candies of high quality.

The CVT, which is white in color, non toxic and edible, is the solid fat of the seed of the Chinese Tallow tree, encapsulating the internal shell of the kernel seed. The Chinese Tallow Trees (Sapium sebiferium L. Roxb) is of Chinese origin and grows in vast numbers in most of the provinces of China. They cover the subtropic and warm-temperature zone. Their total fat output per acre is higher than that of the oil palm (Elaeis guinensis). The Chinese Tallow Tree has been introduced into the southern coastal region of the U.S. and it may be possible to cultivate it over the world. Research for the development of the Chinese Tallow Tree is the focus of attention in U.S., India, Pakistan, U.K., Japan and Brazil. The CVT contains rich triglycerides with oleic acid radicals located in the B-position. It is a cheap and abundant raw material for CBE in China specifically.

However, the type of seeds mentioned above contain both solid fat (CVT) and a liquid oil (Stillingia oil). The Stillingia oil is toxic and unedible. Therefore, in an industrial production of CVT it is necessary to use suitable processing and technology, and to control the quality of CVT to insure the purity of CVT and the stability of CBE quality.

Recently, two experimental methods of manufacturing Cocoa Butter Equivalent (CBE) from Chinese Vegetable Tallow (CVT) as the starting material have been proposed. In one method, raw CVT is treated with acetone or #8 light gasoline, crystallized for 3 to 6 hours, filtered under constant temperature and, after removing the solvent under reduced pressure from the product, the product is refined using three processes (i.e. deacidification, decolorization and deodorization (steam distillation)). The second process begins with CVT which has been refined (using the steps of deacidification, decolorization and deodorization), then dissolved in organic solvents (acetone or #8 light gasoline), crystallized, filtered under constant temperature, and the solvent removed from the product-containing filtrate under reduced pressure. The efficiency of a method of fractional crystallization using raw CVT as a starting material would be affected by the presence of large amounts of impurities.

The CBE product obtained when using refined CVT as a starting material but no after treatment may be contaminated with introduced impurities, moisture, residual solvents, etc. Also, solvent and energy consumption in removing solvents such as acetone or #8 light gasoline is high. Further, the crystallization processes are long and the quality of product if low.

The literature concerning the above process does not indicate any quality specifications nor any test means. The raw CVT might be contaminated by toxic materials such as stillingia oil, but no requirements of controlling the stillingia oil are indicated. Since only conventional methods of refining (deacidification, decolorization and deodorizing) are used without any indication of toxicity test on experimental animals, the edibility of the product cannot be insured.

SUMMARY OF THE INVENTION

Therefore, the purpose of this invention is to provide a process for producing CBE with reliable security of edibility, high yield, high quality and low cost.

For the purpose mentioned above, in order to strictly control the purity of raw CVT, a special semi-refining technique, a fractional crystallization technique, and a post-treatment as well as a crystallization column of special structure are employed. In the process, the choice of solvent and the ratio of starting material to solvent, the use of solvent recovery system under atmospheric pressure, the selection of a cooling rate and speeds of stirring in different stages of crystallization, the design of the crystallization column, the determination of various parameters, and the means for reducing the solvent consumption and energy consumption are all well-considered, so as to raise the yield and quality of CBE. Its SFC% (solid fat content) curve is comparable to that natural cocoa butter. Furthermore, the process is simple and the production period is short. It is also easy to practice and to expand application with low investment and cost, and with high economic efficiency. Especially the non-routine "three stages of refinements" technique involved in the course of semi-refining adsorption for removing impurities and post-treatment in this invention makes the CBE product safely edible as shown by toxicity test on experimental animals.

BRIEF DESCRIPTION OF THE DRAWING

The detail descriptions will be given referring to the respective figures as follows.

DETAILED DESCRIPTION OF THE INVENTION

Figure 1:
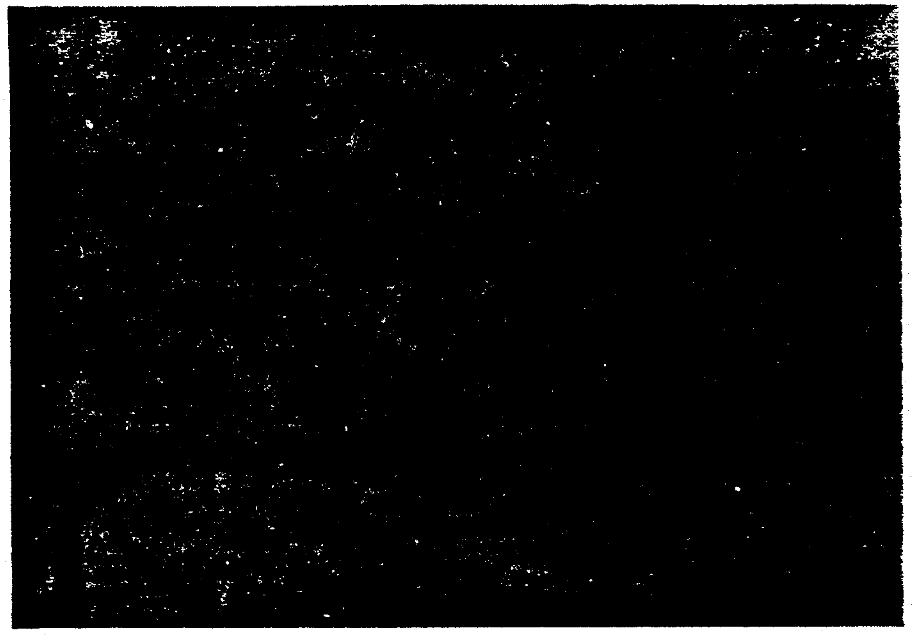
FIG. 1: A micro-polariscopic color photo of the solution at 28° C. (enlarged by 6000).

The apparatus as shown is directed to a batch process. The column (1) contains stirrer (3) along most of its length. The stirrer is activated by motor driven system, (2) which includes installations for speed variations, such as gears. A circulating pump (4) is used to mix semi-refined CVT and appropriate solvent at the beginning of a run and to insure a consistent solution of a consistent temperature at the start of a run. Tanks (5) are used to prepare refrigerants. In this diagram, 4 separate tanks are shown. Pump (6) pumps the refrigerants from the various tanks to various inlets (7) in the jacketed column. Outlets (8) return the refrigerant to the refrigerant tanks Pipe (9) is an inlet for refrigerant from a refrigerant reservoir in a separate area while pipe 10 allows of the return of refrigerants to the refrigerant reservoir. Materials are discharged at (11) at the bottom of the column and (12) is a by-path for the crystal-mother liquor separator. Item (13) is an inlet for CVT solvent and for solution of CVT. Items (15) and (15) are conventional overflow and venting systems. Items (16) and (17) are various thermometers or temperatures recorders used to monitor temperature. Although 4 tanks are shown for refrigerants, the actual number is not critical. All that is required is that provisions are available for providing cooling liquid to the column at the temperatures required by various steps of the process and that the rate of cooling be controlled at the rates specified. By mixing refrigerants kept at different temperatures at different rates, any desired temperature and rate of cooling can be obtained.

This invention is susceptible to two general modes of implementation. Both modes involve starting with semi-refined CVT, details of which follow at pertinent areas of the specification. A semi-diagrammatic step is:

Process I

Semi-refined CVT→adsorption to remove impurities→single step fractional crystallization separation of the crystals from the mother liquor containing the desired product→recovery of solvent from the mother liquor→post-treatment of the product.

Process 2

Semi-refined CVT→single step fractional crystallization separation of the crystals from the mother liquor containing the desired product→recovery of the solvent from the mother liquor (under atmospheric pressure)→adsorption to remove impurities→post-treatment.

Figure 7:
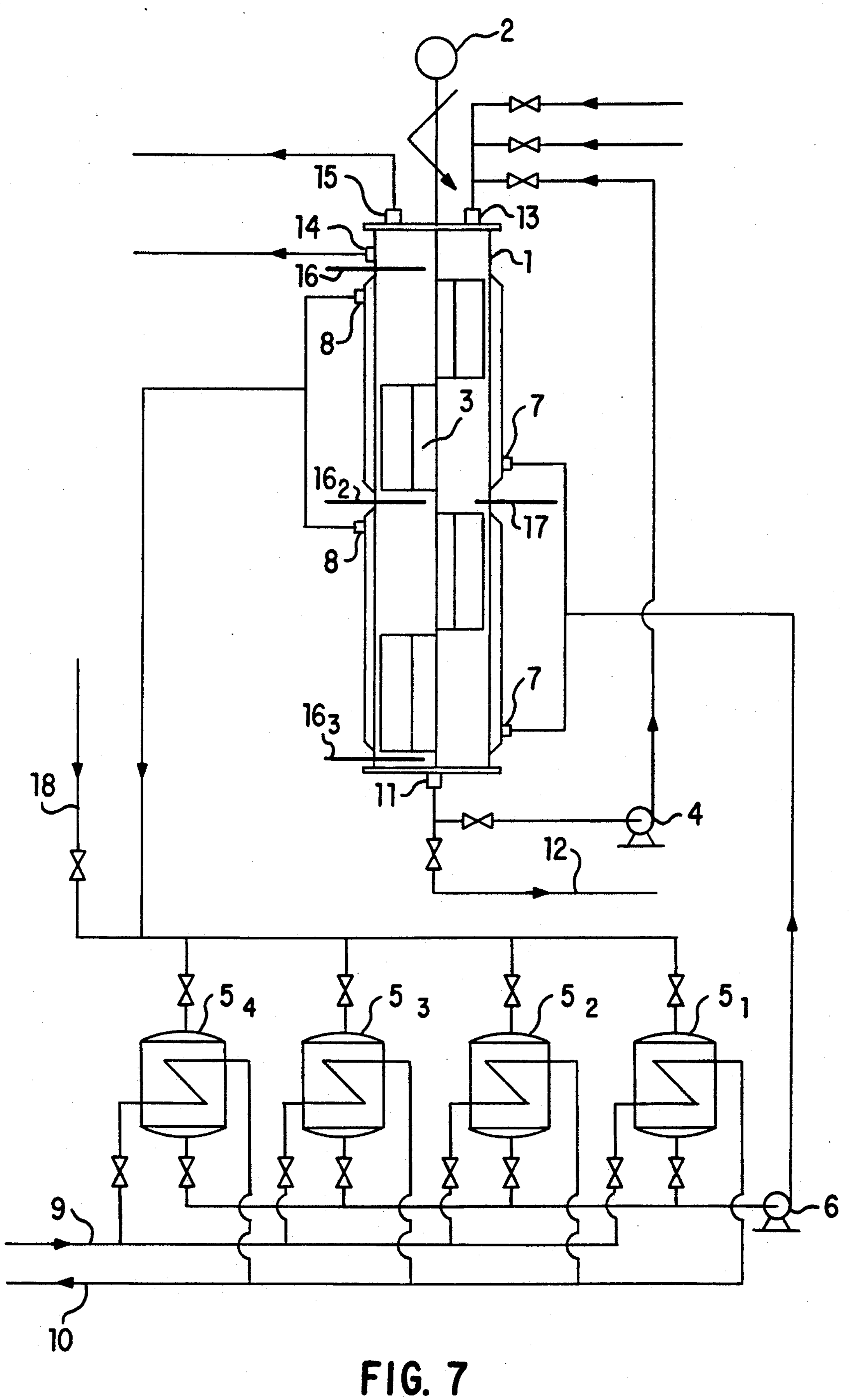
FIG. 7 is a flow schematic diagram of an apparatus for solvent crystallization.

The specific description of Process 1 is as follows:

Semi-refined CVT is maintained at 50° C.-75° in a fractional crystallization column with a specific structure as shown in FIG. 7, after an adsorption treatment. Solvent #6 which is pre-heated to 20°-37° C. in the ratio (starting materials to solvent) of 1:4-1:6 (kg:liter) is added alternatively with the CVT into the column. Then the stirrer is started and stirring is continued for ca.20 minutes at 30°-35° C. so as to form a homogenous phase of oil and solvent. A multi-stage refrigerating fluid system with a temperature range of 1° C. to 33° C. divided into 3 or 4 steps is applied. The crystallization under controlled cooling lasts for 2-4 hours with temperatures between 1° C. and 16° C.. After the crystallization is completed, the crystals are separated from the mother liquor in a crystal separator with a vacuum circuit system (vacuum 600-700 mmHg). The liquid portion is evaporated under atmospheric pressure to recover the solvent. After evaporation, crude CBE is obtained. This is heated by steam, and treated by passing it through a post-treatment system of high-temperature and high-vacuum (maintained for 2-3 hours under 170°-245° C. and residual pressure≦(5 mmHg) and thus a CBE product is obtained. The crystal portion is melted by hot solvent vapor coming from the CBE solvent recovery system, and the by-product obtained in a post-treatment system after evaporation in the by-product solvent recovery system.

In the adsorption step of either process 1 or process 2, the oil temperature is controlled at 85° C.-105° C.. Then 0.5% -2.0% (per oil weight) of activated clay, and 5% -20% (per clay weight) of activated carbon powder is added. The mixture is stirred for 20-40 minutes under vacuum condition (vacuum: CA 700 mmHg). This procedure, serves to absorb impurities. As noted the only difference between process 1 and process 2 is the stage at which this step is implemented.

The raw material used in this invention is chiefly semi-refined CVT in view of added security of edibility. In the process of preparing CVT, flavone glycosides etc. contained in the fruit peel and stem of the tallow tree seed, which may cause acute intoxication, contaminate the raw CVT. Furthermore, some toxic substances in the stillingia oil may also contaminate the raw CVT during the procedure of breaking off the solid fat covering the seeds or during a procedure of solvent extraction. Therefore, techniques used to produce nontoxic raw CVT are needed, to insure the rationality of the method of preparing CBE from raw material. Obviously, it is irrational to let toxic stillingia oil mingle uncontrollably and then take measures to remove it. Thus the starting material CVT has to be examined strictly for controlling its purity and insuring the stability of the quality of CBE simultaneously. As stillingia oil contains highly unsaturated fatty acids with short carbon chains, and is rarely seen among other natural vegetable oils and fats, it is easily oxidized owing to its high unsaturation. Hence, mingling of the stillingia oil will surely lead to deterioration of CVT and CBE, and make CBE and CBE chocolate products lose their original commodity value. Also there are other factors which may cause deterioration of CVT and CBE, such as the absence of natural antioxidants, such as vitamin E, etc., in the CVT.

Analysis of the composition of fatty acid in stillingia oil shows that linolenic acid (C 18:3) is the constituent of the highest content. Therefore, in this invention, the linolenic acid content is considered as the indicator of existence of stillingia oil.

In this invention, C (18:3) in the raw CVT should not exceed 0.1%.

Testing device: Gas Chromatograph.

Calculation of content: Area Normalization Method.

Conditions for test:

Column: 3 mm I.D. X 2M glass column packed with 6% DEGS on 60-80 mesh chromosorb W AW-DMCS Detector: flame ionization detector Column Temperature: 185° C.

Injection port temperature: 230° C.

Carrier gas: nitrogen, 30 ml/min.

Integrator attenuation: G

Sample volume: 0.2 u ml

In this invention, not only is the purity of raw CVT strictly controlled, the acid value of semi-refined CVT is also controlled. If the acid value of the semi-refined (or wholly refined) CVT is high, the acid value of CBE will also be high. The presence of excessive free fatty acid in CBE will not only give rise to irritation and a paraffin odor taste in the mouth, it will also produce aldehydes and ketones after deterioration. In order to meet the requirements of secure edibility, it is necessary to apply semi-refining technique other than the ordinary method of de-acidification and de-colorization.

The semi-refining procedures and conditions found to be necessary are:

1) An alkali treatment. During this process, the temperature of the CVT oil should be kept at 60° to 65° and the temperature of aqueous NaOH should be kept at 30° to 35° C. The concentration of the NaOH is preferably 14° to 17° Baume'. The concentrations is not highly critical but since fairly high temperatures are used, excessive concentrations of NaOH should be avoided.

The concentrations should be adjusted in order to permit removal of natural acids present without causing hydrolysis or decomposition of any desired products present in the oil. The temperatures not only suit the feature of the high melting point of CVT, but also make granule particles formed in the processing coarse and large, and easily precipitated. Thus high efficiency of separation will be attained. The rest of the operative conditions are taken according to alkali treatment methods commonly used.

2) A salt water washing process. During this procedure, the temperature of the oil in the first washing should be kept at 85° to 95° and a boiling NaCL solution (0.05 to 0.2% NaCl by weight) is used. A concentration of about 0.1% is preferred. The volume of salt solution used is about 15% to 30% of the CVT oil volume (about 20% being preferred). Chemical substances such as flavone glucosides that can contaminate the CVT oil can be removed. Following the first wash several washes are made with the boiling salt water using the indicated ratios of water and oil. The oil is then subjected to a vacuum process to remove excess water. The rest of the operative conditions are taken according to methods of water-washing commonly used.

The main purpose of the adsorption step is not for decolorization but to take off residual particles after possible saponification by NaOH, and to remove residual insecticides so as to insure the security of edibility. If insecticides have not been sprayed during the growth period of the tallow tree seed, then the activated carbon treatment may be omitted. (The rest of the operative conditions are taken according to adsorptions method commonly used.)

The organic solvent used for the fractional crystallization in this invention is #6 solvent, viz. Petroleum ether of distilling range 60° C.–90° C. Utilization of different distillation range of petroleum ether may result in requiring different temperatures and will give different yields. This #6 solvent is commonly employed in the oil and fat industry, because of its low price, abundant source, and moderate temperature range. More importantly, when this solvent is employed in food processing, it must meet the strict requirements of food sanitation. Actually, petroleum ether is the only organic solvent permissible in food processing trades under the regulations on food sanitation in many countries.

The organic solvent employed in this invention may also be acetone, iso-propanol, mixed solvent of acetone-alcohol (the volume of alcohol less than 30%), and petroleum ether of different distillation ranges, e.g. petroleum ether of 30° C.–60° C., 60° C.–70° C., 60° C.–90° C. (n-hexane is the petroleum ether with distillation temperature of about 68° C.). But the crystallization technical parameters such as temperature, time etc. must then be changed correspondingly. On entirely coordinated considerations of the price, resources, consumption of the solvent, alteration of distillation range or intermingling ratio after multi-stage recycling, security of edibility and the present situation of the oil and fat trade of China, the petroleum ether of 60° C.–90° C. in distillation range is preferable.

The ratio of starting material to solvent used in this invention may be 1:1 to 1:7 (weight:liter). If the ratio of the solvent to raw material is too low, the crystallization time is prolonged with low fractionation efficiency, and poor quality of product. But if the ratio of the raw material to solvent is too high, the consumption of solvent and energy would render the costs too high. Different ratios of starting material to solvent may result in corresponding alterations of crystallization temperatures and times.

The procedures and conditions for the single step crystallization fractionation in this invention are as follows:

1. Pre-heated input

The semi-refined CVT is pre-heated to 50° C.–75° C., and #6 solvent is pre-heated to 20° C.–37° C. The starting material and the solvent in the ratio of 1:4–1:6 (kg:liter) are put into the crystallization column alternatively several time to mix the oil with the solvent homogeneously in order to reduce the longitudinal temperature difference between the upper part of the solution and the lower part of the solution in the column and to prevent the formation of fat particles. Then the stirring system is started and the whole system is cooled down.

2. Heat-retaining stirring

When the solution is cooled to 35° C.–32° C., it is stirred at constant temperature for about 10–40 minutes. The importance of the step lies in the following, first the solution will be made homogeneous, and also the temperature difference between the upper part and the bottom part of column will be reduced to the permitted range ($\Delta T < 2°$ C.); secondly, fine fat particles possible present in the solution may be eliminated: and third, the efficiency of fractionation may be increased by controlling the formation speed of crystal nuclei to produce fewer but larger crystal centers.

(Before the solution has been cooled to 28° C., the nuclei appear as shown on the micropolariscopic photo of FIG. 1).

Referring to FIG. 1, in the solution under this specification condition (e.g. the ratio of starting material to solvent is 1:5, and the cooling rate is 0.4° C./min. (the crystal nuclei may appear at 28° C. As this photo is magnified by 6000-fold, the nucleus formation is through to begin above 28° C.

3. Cooling crystallization

After heat-retaining stirring, the multi-stage refrigerating liquid system (i.e. refrigerating liquid system at different temperature ranges) can be used to perform fractional crystallization. The temperature-decreasing rate in the cooling crystallization is strictly controlled in this invention. The temperature-decreasing rates in different stages are as follows:

The temperature decreasing rate in the solution stage:0.5° C./min. –1.5° C./min., wherein 1.0° C./min. is preferable, The temperature-decreasing rate in nucleus formation stage:0.1° C./min.–0.6° C./min. wherein 0.3° C./min. is preferable, The temperature-decreasing rate in crystal growth stage:0.1° C./min.–1.0° C./min. wherein 0.6° C./min. is preferable, The temperature-decreasing rate is calculated every ten minutes.

The multi-stage refrigerating system (i.e. cooling liquid of difference temperature) is used in this invention for controlling the temperature decreasing rate. The refrigerating process may be divided into four or three stages. The total temperature range of the refrigerating liquid is 1° C.-33° C.

The temperature of refrigerating liquid in four stages are as follows:

The temperature of refrigerating liquid in the first stage is 33° C.-30° C. wherein 31° C. is preferable.

The temperature of refrigerating liquid in the second stage is 20° C.-10° C. wherein 15° C., more or less, is preferable.

The temperature of refrigerating liquid in the third stage is 10° C.-5° C. wherein 8° C., more or less, is preferable.

The temperature of refrigerating liquid in the fourth stage is 5° C.-1° C. wherein 3° C., more or less, is preferable.

The temperatures of refrigerating liquid in three stages are as follows:

The temperature of refrigerating liquid in the first stage is 33°-30° C.° C. wherein 31° C. is preferable.

The temperature of refrigerating liquid in the second stage is 15° C.-8° C. wherein 12° C. is preferable. The temperature of refrigerating liquid in the third stage is 8°-1° C., wherein 5° C. is preferable. Other multiple temperature range of refrigerating liquid that can insure various temperature-decreasing rate may also be employed. But the total temperature range should be determined according to the desired final temperature of the cooling crystallization.

The control of flow rate of refrigerating liquid in controlling temperature-decreasing rates by refrigerating liquid is also of utmost importance.

The importance of controlling the temperature-decreasing rate has been proven by micropolariscopic photos. Properly controlled temperature-decreasing rates result in coarse crystals, high efficiency of fractionation, and easier separation of crystals from the solution. In contrast, improper control results in a large quantity of fine particles which grow with difficulty, a paste-like crystal solution, low efficiency of fractionation and difficulty in separating crystals from the solution. See FIG. 2 and FIG. 3.

Figure 2:
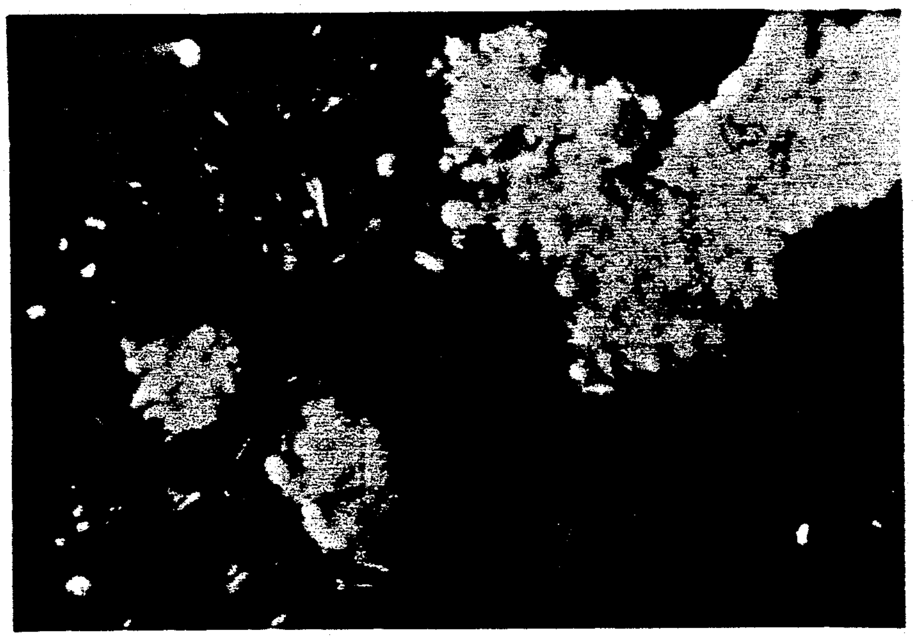
FIG. 2: A micro-polariscopic color photo of the crystals in crystal growing period at a controlled cooling rate (enlarged by 6000).

As shown in FIG. 2, the crystal particles formed are coarse if the temperature-decreasing rate is properly controlled during crystallization, in which the temperature-decreasing rate in nucleus formation stage is 0.4° C./min., the temperature-decreasing rate in the crystal growth stage is 0.1°-0.5° C./min., the temperature-decreasing rate in crystal maintaining stage is 0.1°-0.0° C./min., the crystallization time is 162 min., and the crystallization temperature is 8.° C.

Figure 3:
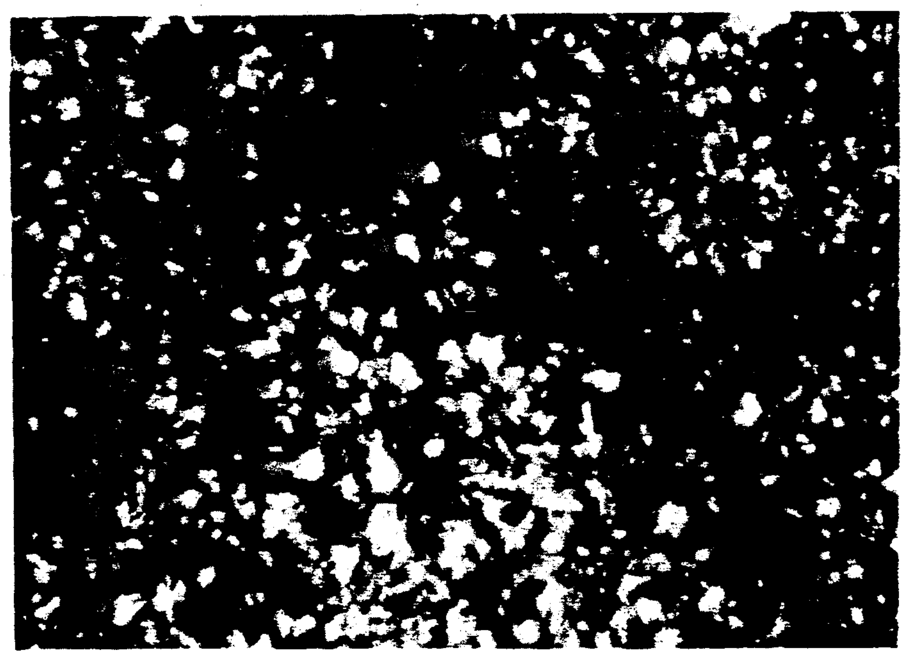
FIG. 3: A micro-polariscopic color photograph of crystals in a late stage of crystallization, in which the cooling rate is out of control.

As shown in FIG. 3, if temperature-decreasing rate is out of control, the crystal solution then becomes paste-like and the efficiency of fractionation is not ideal. FIG. 3 is obtained under the following condition: the temperature is decreased by rapid refrigeration, the duration of crystallization lasts only 93 minutes and the final temperature is 8° C.

As the crystal concentration of the solution in the column increases continuously during cooling crystallization, the stirring speed is then required to be altered to insure the efficiency of heat- conducting (cooling and to prevent the crystals from being damaged by intensive stirring. The stirring speeds in different stages of the temperature-decreasing stage of the solution is 50-20 rpm wherein 30 rpm is preferable.

The stirring speed of the crystal nucleus formation stage is 40-15 rpm; wherein 25 rpm is preferable.

The stirring speed of the crystal growth stage is 30-10 rpm; wherein 16 rpm is preferable.

The stirring speed of the crystal maintaining stage is 20-5 rpm; wherein 8 rpm is preferable.

4. Crystal maintaining by heat-retaining

After cooling crystallization, the crystals should be maintained under heat-retaining conditions to eliminate fine crystals, and to make crystal particles grow larger. After the crystal maintaining has been finished, the material is discharged for separation of the crystals from the solution.

5. Separation of the crystals from the solution. A crystal-solution separation with a vacuum circulation system is used for separating the crystals from the solution by vacuum suction filtration. The vacuum is controlled at the range of 600-700 mmHg. In this procedure, the recovery of solvent from the vapor phase is very important in order to reduce the consumption of solvent. The application of a vacuum system greatly reduces the consumption of solvent, which can be recycled back to various areas of the system.

6. The recovery of solvent in the liquid portion.

Cocoa Butter Equivalent (CBE) is obtained after the recovery of the solvent from the liquid portion.

The PoP content of the CBE obtained is greater than 85%. Pop is a symmetrical triglyceride sometimes called oleodipalmitin. Oleic acid is at position 2 of the glycerol and a $C_{16}$ saturated fatty acid such as palmitic acid is at positions 1 and 3 of the glycerol.

Atmospheric solvent recovery is preferred in this step. Generally, steam is used to stir the solution during evaporation. Steam can be used to heat the tank if desired. The temperature of the evaporation equipment is maintained at about 105° C.

7) Crystal melting and solvent recovery in the crystal portion.

The crystal portion remaining in the crystal separator contains a large amount of PPP. This is a triglyceride of fatty acids where the fatty acids at positions 1, 2 and 3 of the glycerol are saturated $C_{16}$ fatty acids.

The hot solvent or the solvent vapor coming from the CBE solvent recovery equipment may be utilized for melting the crystals. The melted crystals are transferred into a by-product solvent recovery system, and the by-product is then obtained after the solvent has been evaporated. The temperature in the solvent recovery equipment is controlled at about 105° C. Steam provides heat energy.

Thin film evaporators and stripping columns can be used as the main equipment of the solvent recovery system on a large scale of production, while thin film evaporator and evaporation stills are adopted on a small scale of production. The CBE and its by-products after evaporation enter into the post-treatment systems separately.

The crystallization lasts 2-4 hours including crystal maintaining. The crystallization time is calculated commencing from the time by which the temperature of the solution is reduced to below 35° C. Before this time, it is only a purely physical temperature-decreasing period and no nucleus is formed. The duration of crystal maintaining is calculated commencing from the beginning of temperature-retaining. The duration of crystal maintaining need not to be too long.

The crystallization temperature in this process is higher than 1° C. and less than 16° C. The crystals appear in the column at ca.23° C., and can be seen by the naked eye. As the temperature is cooling down, new phases of crystals may be produced at different temperature points. That is to say, the crystallization temperature ranges from the temperature of nucleus formation of the temperature of crystal maintaining. The crystallization temperature in this invention implies the final temperature of crystallization, viz. the one at the terminal stage of maintaining crystals before discharge. The preferable crystallization temperature is 5.5° C.–8.5° C.

The CBE yield (in weight %) in this invention is greater than 40% and less than 85%. Usually high quality and high yield, are expected in crystallizations. In this invention, 40% is not the low limit; the less the yield, then the more PPP being separated, the less PPP contained in CBE and the better the SFC% value at 35° C. However, the yield cannot be too low, as the melting-point of CBE, and the content of triglyceride structures (SUS) and various unsaturated fatty acids should meet the requirements concerned. SUS means triglycerides where positions 1 and 3 of the glycerol are saturated fatty acid and position 2 is an unsaturated fatty acid. It also can not be too high, The reason is, the higher the yield, the higher the SFC% value, and then the SFC% curve will further depart from the SFC% curve of natural cocoa butter and also the poorer the quality of CBE. And more important is that, the higher the yield, the higher the SFC% value at 35° C. will be. According to the specification for CBE in this invention, the product could not meet its specification if the SFC% value is greater than 7% at 35° C.

To reach a yield over 80%, various parameters in crystallization should be controlled more strictly: and if the yield is below 40%, the CBE chocolate will be a little softer. Therefore, a yield of 60–70% in this invention is preferable.

The procedures and conditions of the post treatments of CBE (and its by-product) in this invention are as follows:

These post-treatments include steam distillation (de-odorization), anti-deterioration and pressurized filtration.

1. Steam distillation

The CBE after evaporation must be distilled. This is commonly called de-odorization. In this process, it is preferable to use steam distillation.

High temperature and high vacuum are employed in this procedure to eliminate any initial flavor in the CBE, to remove decomposed products and minute quantity of residual solvent, so as to meet the specifications of CBE with regard to the taste of the chocolate.

A more important thing is to decompose residual chemical impurities, which may have enter into the CBE under high temperature in order to insure the edibility of CBE products.

Temperature: 170° C.–245° C., are maintained for 2–3 hours.

Vacuum residue pressure≦5 mmHg.

Heating method: The same as deodorization commonly used, except that the oil is heated to about 150° C. with indirect steam, and then with far infra-red electric heating devices.

2. Anti-deterioration procedure

In order to raise the antioxidation ability and the stability of the CBE product, the oil temperature is reduced to less than 110° C. after de-odorization and the proper quantity of antioxidant and stabilizer permitted under food-stuff sanitation requirements, such as edible BHT or vitamin E and edible citric acid, can be added. The oil temperature is then reduced to around 70° C., and the oil is discharged for pressurized filtration.

3. Pressurized filtration

The discharged material should undergo pressurized filtration after distillation (de-odorization) to remove impurities that possibly may come from containers, equipment and pipe lines during handling, transportation, crystallization, separation and solvent recovery steps so to meet the specification of CBE purity and to insure the quality of CBE chocolate.

The starting material employed in the single step solvent cooling fractional crystallization of this invention is semi-refined CVT, but non-refined CVT or wholly-refined CVT may also be employed. However, semi-refined CVT is preferable. When non-refined CVT, i.e. raw CVT, is employed as the starting material for crystallization, the efficiency of fractionation is low and the specifications of quality such as SFC% value etc. are difficult to meet, and the main product (and the by-product) after fractionation must undergo alkali treatment, de-colorizing, and de-odorizing respectively. As the technical conditions of by-product treatment is different from these of raw CVT treatment, two sets of refining equipment are needed to prevent the main product from mingling with the by-product, resulting in high investment costs and high consumption of man-hours and energy, and therefore high total cost. When wholly-refined CVT is employed as the raw material for fractional crystallization, the disadvantages mentioned above will be avoided. But the total quality specification of the product will not be ideal if later operations such as steam distillation, antideterioration treatment and pressurized filtration are omitted. It will be difficult, for example, to reduce the residual solvent to the prescribed limit, if the material has been subjected to steam distillation before hand. It requires two steps of steam distillation, which not only increases the energy consumption but also affects the stability of CBE product.

However, whether non-refined, semi-refined or wholly-refined CVT is employed as the starting material in crystallizing fractionation, all the CBE products are safe in edibility by the process of the present invention. The CBE products must undergo sufficient tests for quality to determine whether they are qualified or not.

The specification of the CBE in this invention are as follows:

1. The content of linolenic acid (C18:3) in the fatty acids of raw CVT should not be over 0.1%.

2. Color: white or slight yellowish white.

3. Odor: odorless

4. Moisture and volatile matter should not be over 0.02%.

5. Impurities should not be over 0.02%

6. Free fatty acid content (calculated as oleic acid) should not be over 0.15%

7. Peroxide value should not be over 0.15%

8. Residual solvent content should not be over 10 rpm.

9. Melting point (mp): 31° C.–35° C.

10. SFC% value, i.e. solid fat content (NMR Method), should be as follows:

$>$85% at 10° C.
$>$80% at 20° C.
$>$74% at 25° C.
$>$52% at 30° C.
$\geqq$7% at 35° C.

11. SUS (S-saturated acid, 0-oleic acid) 65%
12. Unsaturated fatty acid in B-position should be equal or more than 85%
13. Total content of unsaturated fatty acid should be less than 45%
14. Total content of di-unsaturated and poly-unsatured fatty acid should be less than 5.0%
15. Lauric acid should be less than 1.0%
16. Trans-fatty acid should be less than 0.1%
17. Iodine value (wijs method): 28–38.

The CBE product prepared by this invention has, been sufficiently tested for toxicity in experimental animals. The results of the test prove it to be safe in edibility. The toxicity test that have been undertaken are as follows:

1. LD 50 half-lethal doses toxicity test
2 Subacute toxicity test
3. Ames test
4. Mice feeding test for 90 days
5. Micro-nucleus test of poly-stained red cell of bone marrow
6. Deforming test on rats
7. Dominant lethal test In the above-mentioned animal feeding experiments, the samples use in item 1, 2, 3 were prepared in laboratory scale of this invention, and those of the item 4, 5, 6, 7 were prepared in pilot plant scale according to the process of the present invention. The CBE prepared by the above-mentioned method is good in quality with reliable security in edibility. The other advantages of the process are as following: A short technical line and production period; high yields; low cost; high economic efficiency; simple equipment and low investment. It is also easy to expand.

EXAMPLES

EXAMPLE 1

The optimal embodiment of the present invention is referred to the above-mentioned process 1 with the single step of solvent crystallizing fractionation.

Permissible error in temperature: ±1° C.
Permissible error for CBE yield: ±2% (in weight.)
Oil temperature of semi-refined CVT: 65° C.
Quantity of starting material: 90 kg
Quantity of solvent added: 0.15 $m^3$
Stirring time with heat-retaining: 15 min.
Crystallization temperature: 5° C.
Crystallization time: 155 min.
Vacuum in crystal separation: 650 mmHg.
Temperature-decreasing rate of solution: 0.9° C./min.
Temperature-decreasing rate in nucleus formation stage: 0.1°–0.2°/min.
Temperature-decreasing in growth stage of crystal nucleus: 0.1°–1.0° C./min.
Temperature-decreasing rate in crystal maintaining stage: 0.0°–0.1° C./min.
Stirring speed in temperature-decreasing stage of the solution: 30 rpm
Stirring speed in nucleus formation stage: 30 rpm
Stirring speed in growth stage: 30–23 rpm
Stirring speed in crystal maintaining stage: 7 rpm
CBE yield: 57.8% (in weight),
CBE melting point: 31.6° C.
CBE iodine value: 32.36,
CBE saponification value: 200.69.

SFC% value (assayed by Nuclear Magnetic Resonance method) is shown in Table 1:

TABLE 1

| Temperature | 10° C. | 20° C. | 25° C. | 30° C. | 35° C. |
|---|---|---|---|---|---|
| SFC % | 91.37 | 86.56 | 82.10 | 58.33 | 0.39 |

After CBE #1 is mixed with natural cocoa butter, the maximal values of SFC% (assayed by NMR method) at various temperatures are shown in Table 2.

| | SFC % | | | | |
|---|---|---|---|---|---|
| Sample | 10° C. | 20° C. | 25° C. | 30° C. | 35° C. |
| CBE #1 60% CB 1 40% | 88.62 | 80.03 | 70.10 | 39.52 | 2.86 |
| CBE #1 40% CB 1 60% | 87.84 | 76.30 | 67.47 | 39.91 | 2.52 |

The fatty acid composition of triglyceride of CBE #1 is shown in Table 3.

TABLE 3

| Composition | 000 | 001 | 011 | 002 | others |
|---|---|---|---|---|---|
| CBE #1 (mol %) | 2.2 | 90.9 | 2.9 | 3.1 | 1.1 |

Note:
0 - saturated acid
1 - oleic acid
2 - linoleic acid
3 - linolenic acid

Others—include triglycerides of structural types of 111, 012, 112, 022, 003 etc.

The contents of SUS type and various unsaturated fatty acid in CBE #1 are as following:

SUS: 89.71% (S - saturated acid, 0 - oleic acid)
B - unsaturated fatty acid: 91.70%
Total unsaturated fatty acid: 33.26%
Total quantity of di- and poly-unsaturated fatty acid: 1.03%
Lauric acid: 0.09%
Trans fatty acid: 0

EXAMPLE 2

The optional embodiment of the present invention is referred to the single step solvent crystallizing fractionation of process 2.

Permissible errors of temperature and yield are the same as those in example 1,

Oil temperature: 68° C.
Quantity of starting material: 90 kg,
Temperature of solvent: 30° C.
Quantity of solvent added: 0.15 $m^3$
Stirring time with heat-retaining: 20 min.
Crystallization time: 155 min.
Crystallization temperature: 6.5° C.
Vacuum in crystal-separation: 650 mmHg
Temperature-decreasing rate of solution: 1.5/min.
Temperature-decreasing rate in nucleus formation stage 0.4°–0.2° C. /min
Temperature-decreasing rate in crystal maintaining stage: 0.2°–0.1° C./min.

Temperature-decreasing rate in growth stage: 0.4°-0.1° C./min.

Stirring speed in temperature-reducing stage of the solution: 26 rpm,

Stirring speed in growth stage: 26-20 rpm,

Stirring speed in crystal maintaining stage: 8 rpm

CBE yield: 65.5%

Melting point: 33.3 ° C.,

Iodine value: 30.98

Saponification value: 200.11

SFC% value (assayed with NMR method) is shown in Table 4.

TABLE 4

| Temperature | 10° C. | 20° C. | 25° C. | 30° C. | 35° C. |
|---|---|---|---|---|---|
| SFC % | 92.36 | 87.77 | 84.31 | 62.69 | 3.70 |

After CBE #2 is mixed with natural cocoa butter, the maximal values of SFC% (assayed by NMR method) at various temperatures are shown in Table 5.

TABLE 5

| | SFC % | | | | |
|---|---|---|---|---|---|
| Sample | 10° C. | 20° C. | 25° C. | 30° C. | 35° C. |
| CBE #2 60% CB 2 40% | 88.82 | 79.13 | 68.91 | 42.66 | 3.60 |
| CBE #2 40% CB 2 60% | 87.97 | 78.18 | 68.84 | 43.11 | 3.41 |

The fatty composition of triglyceride of CBE #2 is shown in Table 6.

TABLE 6

| Composition | 000 | 001 | 011 | 002 | others |
|---|---|---|---|---|---|
| CBE #2 (mol %) | 3.7 | 91.8 | 1.9 | 2.2 | 0.4 |

Note:
0 - saturated acid
1 - oleic acid
2 - linoleic acid
3 - linolenic acid

Others—include triglyceride of structural types of 111, 012, 112, 022, 003 etc.

The contents of SUS type and various unsaturated fatty acid in CBE #2 are as following:

SUS: 90.60% (S - saturated acid, 0 - oleic acid)

B - unsaturated fatty acid: 91.96%

Total unsaturated fatty acid: 32.60%

Total quantity of di- and poly-unsaturated fatty acid: 0.73%

Lauric acid: 0.1%

Trans fatty acid: 0

EXAMPLE 3

The optional embodiment of the present invention is referred to the above-mentioned process 2 with single step solvent crystallizing fractionation.

Permissible errors of temperature and yield are the same as this in example 1,

Oil temperature: 70° C.

Quantity of starting material: 90 kg,

Temperature of solvent: 29° C.

Quantity of solvent added: 0.45 $m^3$

Stirring time with heat-retaining: 20 min.

Crystallization time: 135 min.

Crystallization temperature: 11.5° C.

Vacuum in crystal-separation: 650 mmHg

Temperature-decreasing rate of solution: 1.00° C./min.

Temperature-decreasing rate in nucleus formation stage 0.4°-0.5° C. /min

Temperature-decreasing rate in growth stage: 0.9°-0.1° C./min.

Temperature-decreasing rate in crystal maintaining stage: 0.1°-0.0° C./min.

Stirring speed in temperature-reducing stage of the solution: 26 rpm,

Stirring speed in nucleus formation stage: 26 rpm

Stirring speed in growth stage: 26-20 rpm,

Stirring speed in crystal maintaining stage: 18 rpm,

CBE yield: 82.6%

Melting point: 33.7° C.,

Iodine value: 30.04

Saponification value: 202.55

SFC% value (assayed with NMR method) of CBE #3 is shown in Table 7.

TABLE 7

| Temperature | 10° C. | 20° C. | 25° C. | 30° C. | 35° C. |
|---|---|---|---|---|---|
| SFC % | 93.36 | 89.31 | 85.79 | 64.94 | 6.00 |

After CBE #3 is mixed with natural cocoa butter, the maximal values of SFC% (assayed by NMR method) at various temperatures are shown in Table 8.

TABLE 8

| | SFC % | | | | |
|---|---|---|---|---|---|
| Sample | 10° C. | 20° C. | 25° C. | 30° C. | 35° C. |
| CBE #2 60% CB 2 40% | 88.52 | 79.16 | 64.06 | 39.72 | 2.61 |
| CBE #2 40% CB 2 60% | 87.51 | 77.35 | 66.75 | 42.41 | 4.13 |

The fatty acid distribution of stereometic structure (mol %) triglyceride of CBE #3 is referred to Table 9.

TABLE 9

| Structural type | 000 | 001 | 011 | 002 | others |
|---|---|---|---|---|---|
| CBE #3 | 4.0 | 91.0 | 2.0 | 1.9 | 0.3 |

Note:
0 - saturated acid
1 - oleic acid
2 - linoleic acid
3 - linolenic acid

Others—include triglyceride of structural types of 111, 012, 112, 022, 003 etc.

The contents of SUS type and various unsaturated fatty acid in CBE #2 are as following:

SUS: 89.82% (S - saturated acid, 0 - oleic acid)

B - unsaturated fatty acid: 91.12%

Total unsaturated fatty acid: 32.26%

Total quantity of di- and poly-unsaturated fatty acid: 0.63%

Lauric acid: 0.1%

Trans fatty acid: 0

The composition of distillate fraction of recovered solvent after fractionation is shown in Table 10 (Initial boiling point is 68.0° C.)

TABLE 10

| 10 ml | 20 ml | 30 ml | 40 ml | 50 ml |
|---|---|---|---|---|
| 72.0° C. | 73.0° C. | 73.5° C. | 74.0° C. | 75.0° C. |
| 60 ml | 70 ml | 80 ml | 90 ml | 91 ml |

TABLE 10-continued

| 76.5° C. | 79.0° C. | 85.0° C. | 90.0° C. | 93.0° C. |
|---|---|---|---|---|

The SFC% values of examples 1 to 3 compared with those of natural cocoa butter and Japan FANTOM-500 are shown in Table 11.

TABLE 11

| | SFC % | | | | |
|---|---|---|---|---|---|
| Sample | 10° C. | 20° C. | 25° C. | 30° C. | 35° C. |
| F-500 | 85.0 | 78.8 | 66.6 | 40.0 | 0.1 |
| CB | 90.0 | 88.0 | 81.0 | 66.0 | 0 |
| CBE #1 | 91.37 | 86.56 | 82.10 | 58.33 | 0.39 |
| CBE #2 | 92.36 | 87.77 | 84.31 | 62.69 | 3.70 |
| CBE #3 | 93.36 | 89.31 | 85.79 | 65.94 | 6.08 |

Figure 4:
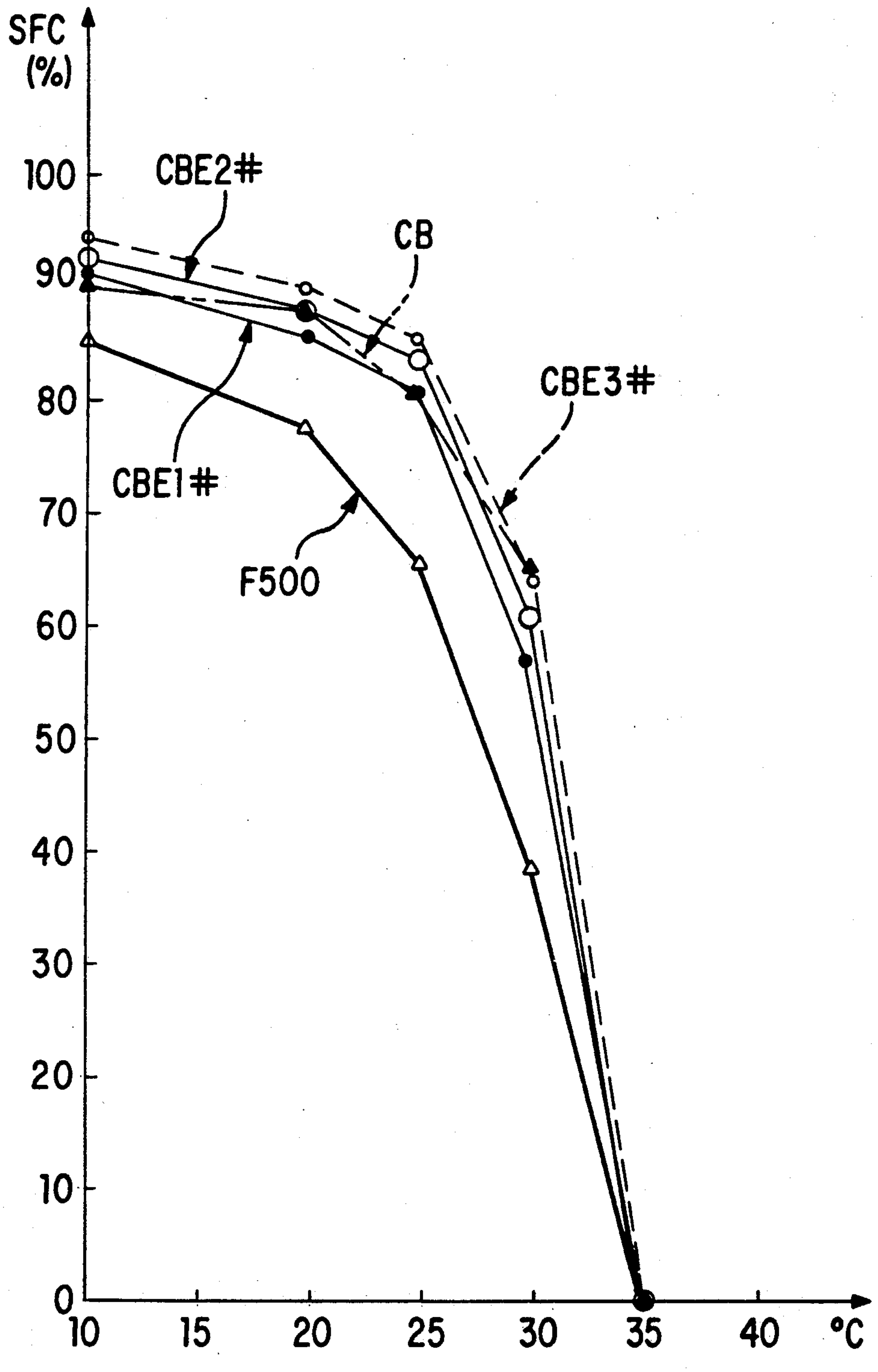
FIG. 4: Comparison of SFC% curves of CBE in examples 1, 2, and 3, to those of natural cocoa butter and Japan Fantom-500.

The comparison of the curves of SFC% value of CBE #1, #2 and #3 to those of natural cocoa butter and Japan FANTOM-500 is shown in FIG. 4. The FIG. 4 shows that the SFC% curve of the CBE prepared by this invention is very close to those of natural cocoa butter.

Note: In FIG. 4, CB denotes the SFC% value curve of natural cocoa butter, and F-500 denotes the SFC% value curve of FANTOM-500. Both of them are the literature values.

Figure 5:
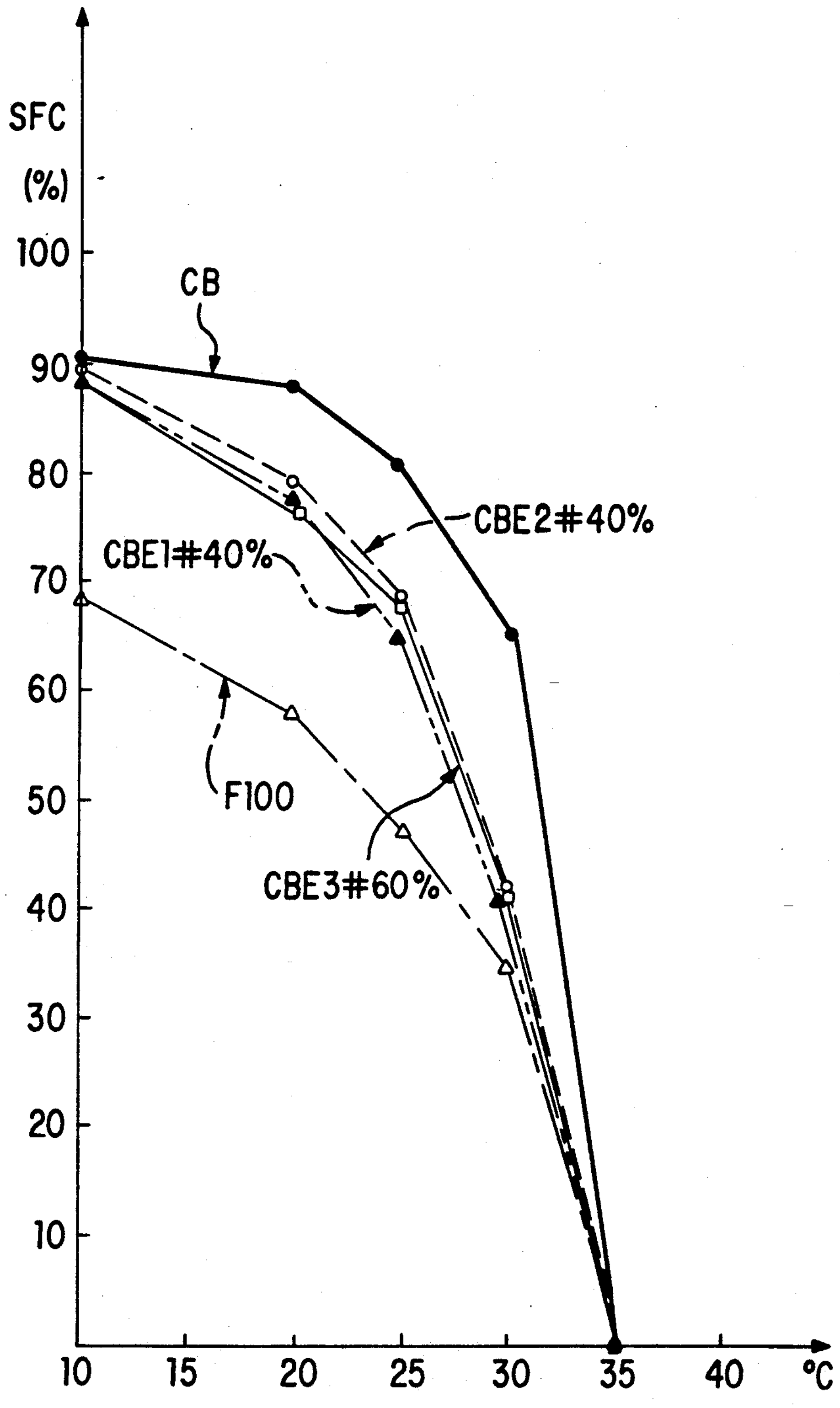
FIG. 5: Comparison of curves of the maximal downfall SFC% values in CBE compatibility data of examples 1, 2, and 3, to those of natural cocoa butter and Fantom-100.

The SFC% down-fall maximums in compatibility data of examples 1, 2 and 3 together with those of natural cocoa butter and FANTOM-100, are shown in Table 12. FIG. 5 shows the SFC%-temperature relation of examples 1-3 together with natural cocoa butter and FANTOM-100 for comparison.

TABLE 12

| | SBC % | | | | |
|---|---|---|---|---|---|
| Sample | 10° C. | 20° C. | 25° C. | 30° C. | 35° C. |
| CB | 90.00 | 88.00 | 81.00 | 66.00 | 0 |
| F-100 | 68.3 | 57.9 | 48.4 | 35.2 | 1.9 |
| CBE #1 40% CB 1 60% | 87.84 | 76.36 | 67.47 | 39.91 | 2.52 |
| CBE #2 40% CB 2 60% | 87.97 | 78.10 | 68.04 | 43.11 | 3.41 |
| CBE #3 60% CB 3 40% | 88.52 | 77.16 | 65.06 | 39.72 | 2.62 |

From FIG. 5, it can be seen that in compatibility data of CBE prepared by this invention, the maximal down—fall value curve of SFC% is still within the range of those of CB and F-100. It proves that the CBE prepared by this invention is compatible with natural cocoa butter in any ratio. Even though natural cocoa butter is completely replaced by the CBE prepared in accordance with this invention, chocolate production can be satisfied.

The comparison of the CBE products of examples 1-3, to those of natural cocoa butter and (represented by CB, cited from literature) those proposed by foreign countries (represented by CBE) are shown in Table 13.

TABLE 13

| | Samples | | | | |
|---|---|---|---|---|---|
| Items | CBE #1 | CBE #2 | CBE #3 | CB | CBE |
| SUS % | 89.71 | 90.60 | 89.82 | 79.0 | ≧65 |
| B - unsaturated fatty acid % | 91.70 | 91.96 | 91.12 | 94.5 | ≧85 |
| Total unsaturated fatty acid % | 33.26 | 32.60 | 32.26 | 34.5 | ≦45 |
| Di-, and poly-unsaturated fatty acid % | 1.03 | 0.73 | 0.63 | 2.5 | ≦5 |
| Lauric acid % | 0.09 | 0.10 | 0.10 | 0 | ≦1.00 |
| Trans fatty acid % | 0 | 0 | 0 | 0 | ≦2.0 |

Figure 6:
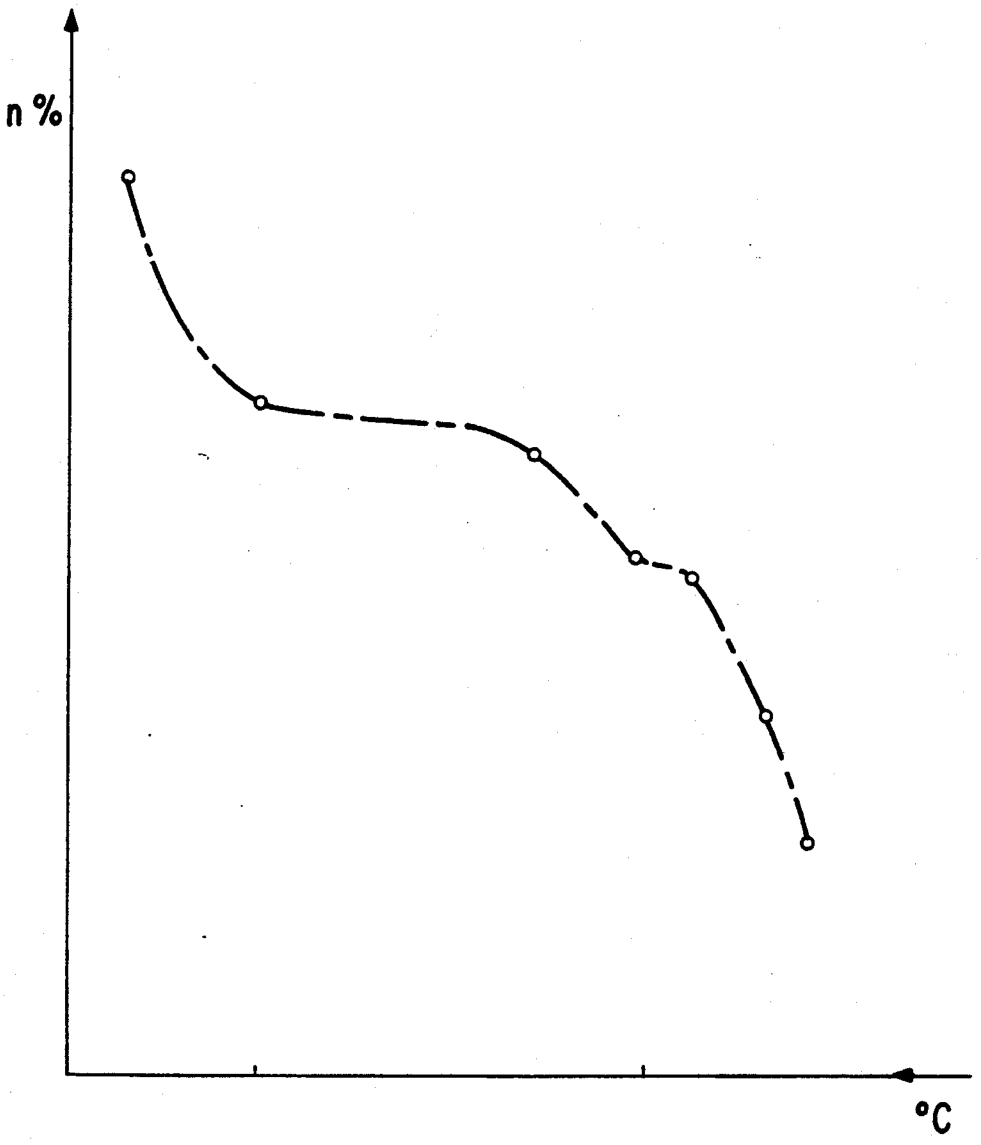
FIG. 6: The curves of CBE yield (in weight %) vs. crystallization temperature (° C.), n=(T).

The relative curve, n=f(T), of the CBE percent yield, n% (in weight) to crystallization temperature (° C.) is shown in FIG. 6.

Permissible error of temperature: ±1° C.

Permissible error of CBE percent yield (in weight): ±2° C.

In FIG. 6, specific temperature degrees and yield are not indicated on the co-ordinate axes, because the solvents used in crystallization may be different. The distillation range or the ratio of starting material to solvent may also be different, even if the same petroleum ether is used. Thus the crystallizing temperature and yield would be different too. But the feature of this curve of crystallization can be seen clearly, i.e. there is a corresponding smooth segment in a rather wide temperature range. The feature is determined by the specific fatty acid component of triglyceride of CVT.

I claim:

1. A process for preparing Cocoa Butter Equivalent (CBE) from Chinese Vegetable Tallow (CVT), comprising the steps of:

a) pre-treating said CVT by:

maintaining said CVT at 55°-65° C.;

alkali refining said CVT with an alkali solution maintained at 30°-35° C.;

washing said alkali refined CVT with 0.05-0.1% concentration boiling salt water;

absorbing impurities out of said washed CVT with 0.5-1.0% (by oil weight) white clay to obtain semi-refined edible CVT;

b) crystallizing said semi-refined CVT by:

maintaining said semirefined CVT 60°-65° C.;

dissolving said semirefined CVT in petroleum ether which is maintained at 60°-90° C., maintaining the ratio of solvent to solute at the range of 1:1.5-1:6.5 (by weight volume);

crystallizing the CVT solution in a single factional crystallization process intermittently between the temperature of 25°-35° C. and 5°-15° C. for a period of 120-180 minutes, wherein the entire crystallization is completed in a single crystallization tower, said crystallization process comprising a first temperature-decreasing-stage, a second nucleus formation stage, a third crystal growth stage, a fourth crystal maintaining stage, wherein temperature rates of the crystallization are controlled by refrigeration liquid, and wherein different stirring speeds are used in said stages of said crystallization process, wherein the temperature of the CVT solution is decreased at said stages at the rate of:

i) 0.5°-1.5° C. per minute at said first temperature-decreasing-stage;

ii) 0.1°–0.6° C. per minute at said second nucleus formation stage;

iii) 0.1°–1.0° C. per minute at said third crystal growth stage, iv) 0.0°–0.2° C. per minute at said fourth crystal maintaining stage, wherein the temperature decreasing rate is calculated every ten minutes;

wherein the temperature of the refrigerating liquid ranges from 33° C. to 30° C. at said first stage, 20° C. to 10° C. at said second stage, 10° C. to 5° C. at said third stage, and 5° C. to 1° C. at said fourth stage; and wherein said refrigerating liquid is multi-stage refrigerating liquid and is used to control the speed of the temperature decreasing rate at every stage and to lower the rate of the stirring speed for successive stages of said crystallization process;

after crystallization, separating the crystal solution by vacuum filtration to obtain crystalline filter cake and a first filtrate;

dissolving said crystalline filter cake with petroleum ether vapor and removing the solvent to obtain a by-product of a high melting point filtrate which does not comprise said CBE; and removing the solvent from said first filtrate; and c) post treating said first filtrate to obtain the desired CBE by:

deodorizing said first filtrate with steam distillation at temperature of 170°–245° C. and under a vacuum of 5 mmHg to obtain a final product yield of at least 50% CBE.

2. The process according to claim 1, wherein said alkali solution is an aqueous sodium hydroxide solution of 14° to 17° Baume' held at 30° C. to 35° C. while the temperature of the CVT is held at 55° C. to 65° C. and wherein said salt water is approximately 0.1 percent concentration of sodium chloride.

3. The process according to claim 1, wherein the stirring speeds used in different stages of the single fractional crystallization in a single crystallization tower are 50 to 20 rpm at the first stage; 40 to 15 rpm at the second stage; 30 to 10 rpm at the third stage; and 20 to 5 rpm at the fourth stage.

4. The product prepared by the process of claim 1 having the following characteristics.

(1) Color: White or slight yellowish white (2) Odor: Odorless (3) Moisture and volatile matter: ≦0.02%

(4) Impurities: ≦0.02%

(5) Free fatty acid content (calculated as acid) ≦0.15%

(6) Melting point (mp): 31°–35° C.

(7) SFC% (solid fat content) (by NMR method) as follows:

>85% at 10° C.
>80% at 20° C.
>74% at 25° C.
>52% at 30° C.
≦7.0% at 35° C.

(8) Lauric acid <1.0%

(9) Trans fatty acid 0.1%

(10) Iodine value (Wijs method): 28–38

(11) Amount of organic solvent residue ≦10 rpm

(12) Peroxide value ≦0.15%

(13) Linolenic acid (C18:3) content of fatty acids ≦0.1%

* * * * *